United States Patent
Avitabile et al.

(10) Patent No.: US 7,846,955 B2
(45) Date of Patent: Dec. 7, 2010

(54) SALT

(75) Inventors: Barbara Giuseppina Avitabile, Harlow (GB); David O'Sullivan, Loughborough (GB); Richard James Bull, Harlow (GB)

(73) Assignees: AstraZeneca AB (SE); Argenta Discovery Ltd. (GB)

( * ) Notice: Subject to any disclaimer, the term of this patent is extended or adjusted under 35 U.S.C. 154(b) by 0 days.

(21) Appl. No.: 12/523,172

(22) PCT Filed: Feb. 6, 2008

(86) PCT No.: PCT/GB2008/000434

§ 371 (c)(1),
(2), (4) Date: Dec. 24, 2009

(87) PCT Pub. No.: WO2008/096149

PCT Pub. Date: Aug. 14, 2008

(65) Prior Publication Data

US 2010/0093816 A1   Apr. 15, 2010

(30) Foreign Application Priority Data

Feb. 7, 2007   (GB) ................ 0702385.6
Feb. 7, 2007   (GB) ................ 0702416.9

(51) Int. Cl.
*A61K 31/421* (2006.01)
*C07D 263/30* (2006.01)

(52) U.S. Cl. ..................... 514/374; 548/235
(58) Field of Classification Search .............. 514/374; 548/235

See application file for complete search history.

(56) References Cited

FOREIGN PATENT DOCUMENTS

WO   WO 2007/017669   *   2/2007   ............. 548/125

* cited by examiner

*Primary Examiner*—Golam M. M. Shameem
*Assistant Examiner*—Samantha L Shterengarts
(74) *Attorney, Agent, or Firm*—Connolly Bove Lodge & Hutz LLP

(57) ABSTRACT

The invention provides [2-(4-chloro-benzyloxy)-ethyl]-[2-((R)-cyclohexyl-hydroxy-phenyl-methyl)-oxazol-5-yl-methyl]-dimethyl-ammonium napadisylate, pharmaceutical compositions containing it, and its use in therapy.

20 Claims, 1 Drawing Sheet

Figure 1: XRPD for 'Salt Form A of [2-(4-chloro-benzyloxy)-ethyl]-[2-((R)-cyclohexyl-hydroxy-phenyl-methyl)-oxazol-5-ylmethyl]-dimethyl-ammonium hemi-naphthalene-1,5-disulfonate
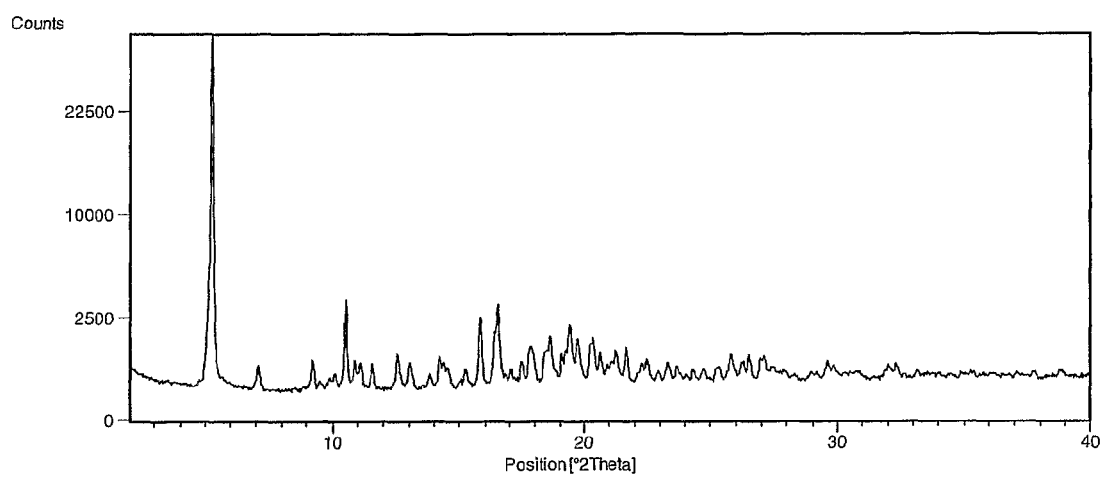

SALT

This patent is a US National Stage under 35 U.S.C §371 of International Application No. PCT/GB2008/000434 (filed 6 Feb. 2008; and published as WO2008/096149 on 14 Aug. 2008), which, in turn, claims priority to GB Patent Application Nos. 0702385.6 (filed 7 Feb. 2007) and 0702416.9 (filed 7 Feb. 2007). The entire text of each of the above-referenced patent applications is incorporated by reference into this patent.

The present invention relates to a salt of a muscarinic antagonist, pharmaceutical composition containing it and its use in therapy.

Muscarinic receptors are a G-protein coupled receptor (GPCR) family having five family members $M_1$, $M_2$, $M_3$, $M_4$ and $M_5$. Of the five muscarinic subtypes, three ($M_1$, $M_2$ and $M_3$) are known to exert physiological effects on human lung tissue. Parasympathetic nerves are the main pathway for reflex bronchoconstriction in human airways and mediate airway tone by releasing acetylcholine onto muscarinic receptors. Airway tone is increased in patients with respiratory disorders such as asthma and chronic obstructive pulmonary disease (COPD), and for this reason muscarinic receptor antagonists have been developed for use in treating airway diseases. Muscarinic receptor antagonsists, often called anticholinergics in clinical practice, have gained widespread acceptance as a first-line therapy for individuals with COPD, and their use has been extensively reviewed in the literature (e.g. Lee et al, Current Opinion in Pharmacology 2001, 1, 223-229).

When used to treat respiratory disorders, muscarinic receptor antagonists are typically administered by inhalation. However, when administered by inhalation a significant proportion of the muscarinic receptor antagonist is often absorbed into the systemic circulation resulting in reported side effects such as dry mouth. Additionally, the majority of muscarinic antagonists have a relatively short duration of action requiring that they be administered several times a day. Such a multiple-daily dosing regime is not only inconvenient to the patient but also creates a significant risk of inadequate treatment due to patient non-compliance associated with the frequent repeat dosing schedule. There therefore remains a need for novel compounds that are capable of blocking muscarinic receptors. In particular, a need exists for new muscarinic antagonists that have high potency and reduced systemic side effects when administered by inhalation. Moreover, a need exists for new muscarinic antagonists that exhibit a long duration of action when dosed by inhalation, and which are amenable to either once or twice daily dosing.

In the manufacture of pharmaceutical formulations, it is important that the active compound is in a form in which it can be conveniently handled and processed in order to obtain a commercially-viable manufacturing process. In this connection, the chemical stability and the physical stability of the active compound are important factors. The active compound, and formulations containing it, must be capable of being effectively stored over appreciable periods of time, without exhibiting any significant change in the physico-chemical characteristics (e.g. chemical composition, density, hygroscopicity and solubility) of the active compound.

Furthermore, if the active compound is to be incorporated into a formulation for pulmonary administration, it is desirable if the active compound can be readily micronised to yield a powder with good flow properties and comprising a high fine crystalline particle fraction (i.e. a fraction in which the active compound particles have a mass median aerodynamic diameter of less than 10 µm (micrometer)). Such a fraction is capable of being carried deep into the lungs leading to faster and increased absorption of the active compound.

International Patent Application WO 2007/017669 (PCT/GB2006/002956) describes a novel class of muscarinic antagonist that display high potency to the M3 receptor. One such muscarinic antagonist described in PCT/GB2006/002956 is [2-(4-chloro-benzyloxy)-ethyl]-[2((R)-cyclohexyl-hydroxy-phenyl-methyl)-oxazol-5-ylmethyl]-dimethyl-ammonium methanesulfonate. The preparation of [2-(4-chloro-benzyloxy)-ethyl][2-((R)-cyclohexyl-hydroxy-phenyl-methyl)-oxazol-5-ylmethyl]-dimethyl-ammonium methanesulfonate described in PCT/GB2006/002956 yields an amorphous solid that is not crystalline and is thus not suitable for micronisation and pulmonary administration. It has now been found possible to prepare an alternative [2-(4-chloro-benzyloxy)-ethyl]-[2-((R)-cyclohexyl-hydroxy-phenyl-methyl)-oxazol-5-ylmethyl]-dimethyl-ammonium salt, which has good physico-chemical properties and which may be suitable for use in a dry powder formulation for pulmonary administration.

Thus, in accordance with the present invention, there is provided a salt which is a napadisylate (naphthalene-1,5-disulfonate) salt of [2-(4-chloro-benzyloxy)-ethyl]-[2-((R)-cyclohexyl-hydroxy-phenyl-methyl)-oxazol-5-ylmethyl] dimethyl-ammonium. In the present specification this salt may be referred to as the 'napadisylate salt'.

The salt of the present invention is herein referred to as [2-(4-chloro-benzyloxy)-ethyl]-[2-((R)-cyclohexyl-hydroxy-phenyl-methyl)-oxazol-5-ylmethyl]-dimethyl-ammonium napadisylate. The name [2-(4-chloro-benzyloxy)-ethyl]-[2-((R)-cyclohexyl-hydroxy-phenyl-methyl)-oxazol-5-ylmethyl]-dimethyl-ammonium was generated by the Autonom 2000 plug in for IsisDraw Version 2.5, as supplied by MDL Information Systems Inc., and denotes the structure depicted in Figure A. Stereochemistry was assigned according to the Cahn-Ingold-Prelog system.

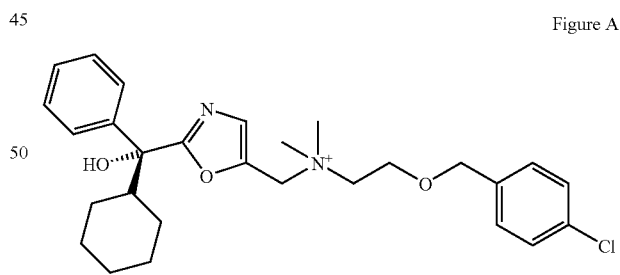

Figure A

The cation/anion ratio in the napadisylate salt of the present invention may vary, and for example may be 1:1 or 2:1 or a value between 1:1 and 2:1.

In an embodiment of the invention, the napadisylate salt has a cation/anion ratio of 2:1, i.e. it is [2-(4-chloro-benzyloxy)-ethyl]-[2-((R)-cyclohexyl-hydroxy-phenyl-methyl)-oxazol-5-ylmethyl]dimethyl-ammonium hemi-naphthalene-1,5-disulfonate, as depicted in Figure B. In the present specification this salt may be referred to as the 'hemi-napadisylate salt'.

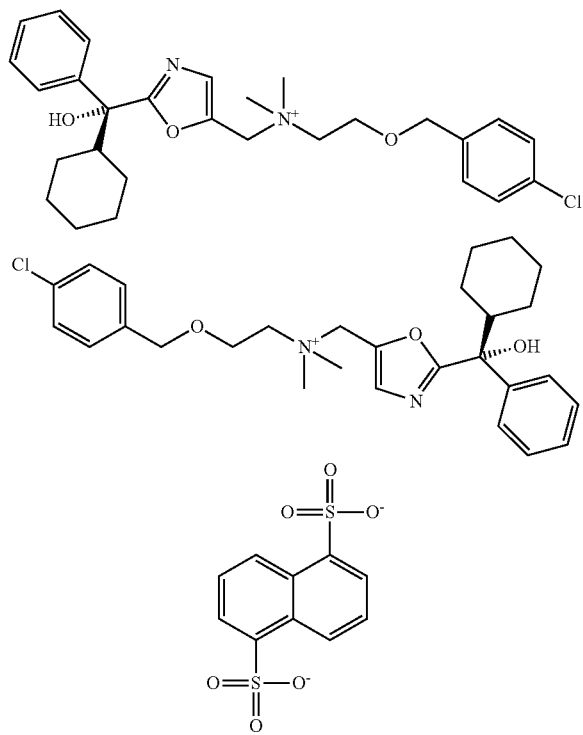

Figure B

The present invention encompasses solvates (e.g. hydrates) of the napadisylate salt.

In an embodiment of the invention, the napadisylate salt has crystalline properties and is preferably at least 50% crystalline, more preferably at least 60% crystalline, still more preferably at least 70% crystalline and most preferably at least 80% crystalline. Crystallinity can be estimated by conventional X-ray diffractometry techniques.

In another embodiment of the invention, the napadisylate salt is from 50%, 60%, 70%, 80% or 90% to 95%, 96%, 97%, 98%, 99% or 100% crystalline.

An example of a crystalline form of [2-(4-chloro-benzyloxy)-ethyl]-[2-((R)-cyclohexyl-hydroxy-phenyl-methyl)-oxazol-5-ylmethyl]-dimethyl-ammonium hemi-naphthalene-1,5-disulfonate is crystalline Form A as defined herein below. Thus, in one embodiment the present invention provides a salt form (Salt Form A) of [2-(4-chloro-benzyloxy)-ethyl]-[2-((R)-cyclohexyl-hydroxy-phenyl-methyl)-oxazol-5-ylmethyl]-dimethyl-ammonium hemi-naphthalene-1,5-disulfonate which exhibits at least the following characteristic X-ray powder diffraction peaks (expressed in degrees 2θ):

(1) 5.3, 10.5, 15.8 and 16.5, or
(2) 5.3, 10.5, 15.8, 16.5, 18.6 and 19.4 or
(3) 5.3, 10.5, 15.8, 16.5, 18.6, 19.4, 19.7 and 20.4 or
(4) 5.3, 10.5, 15.8, 16.5, 17.8, 18.6, 19.4, 19.7, 20.4 and 21.7.

The present invention also provides a salt form (Salt Form A) of [2-(4-chloro-benzyloxy)-ethyl]-[2-((R)-cyclohexyl-hydroxy-phenyl-methyl)-oxazol-5-ylmethyl]-dimethyl-ammonium hemi-naphthalene-1,5-disulfonate having an X-ray powder diffraction pattern comprising specific peaks at 5.3, 7.1, 9.2, 10.5, 10.9, 11.1, 11.6, 12.6, 13.0, 13.8, 14.2, 15.2, 15.8, 16.5, 17.0, 17.4, 17.8, 18.4, 18.6, 19.4, 19.7, 20.3, 20.7, 21.2, 21.7, 22.3, 22.5, 22.9, 23.3, 25.8, 26.5 and 27.1.

In the present specification, X-ray powder diffraction peaks (expressed in degrees 2θ) are measured using copper X-rays with a wavelength of 1.5418 Å. In the present specification unless otherwise stated the margin of error for X-ray powder diffraction peaks (expressed in degrees 2θ) is consistent with the United States Pharmacopeia general chapter on X-ray diffraction (USP941)—see the United States Pharmacopeia Convention. X-Ray Diffraction, General Test <941>. *United States Pharmacopeia,* 25th ed. Rockville, Md.: United States Pharmacopeial Convention; 2002:2088-2089). In an embodiment of the invention, the margin of error for X-ray powder diffraction peaks (expressed in degrees 2θ) is (±0.1°)

FIG. 1 shows an X-ray powder diffraction pattern of Salt Form A of [2-(4-chloro-benzyloxy)-ethyl]-[2-((R)-cyclohexyl-hydroxy-phenyl-methyl)-oxazol-5-ylmethyl]-dimethyl-ammonium hemi-naphthalene-1,5-disulfonate. The present invention also provides a salt form having an X-ray powder diffraction pattern substantially the same as that shown in FIG. 1.

In one embodiment the present invention provides a salt form (Salt Form A) of [2-(4-chloro-benzyloxy)-ethyl]-[2-((R)-cyclohexyl-hydroxy-phenyl-methyl)-oxazol-5-ylmethyl]-dimethyl-ammonium hemi-naphthalene-1,5-disulfonate which exhibits at least the following characteristic d-space values:

(1) 16.8, 8.4, 5.6 and 5.4, or
(2) 16.8, 8.4, 5.6, 5.4, 4.8, and 4.6 or
(3) 16.8, 8.4, 5.6, 5.4, 4.8, 4.6, 4.5 and 4.4 or
(4) 16.8, 8.4, 5.6, 5.4, 5.0 4.8, 4.6, 4.5, 4.4 and 4.1.

The present invention also provides a salt form (Salt Form A) of [2-(4-chloro-benzyloxy)-ethyl]-[2-((R)-cyclohexyl-hydroxy-phenyl-methyl)-oxazol-5-ylmethyl]-dimethyl-ammonium hemi-naphthalene-1,5-disulfonate having an X-ray powder diffraction pattern comprising the following d-space values: 16.8, 12.5, 9.6, 8.4, 8.1, 8.0, 7.7, 7.0, 6.8, 6.4, 6.2, 5.8, 5.6, 5.4, 5.2, 5.1, 5.0, 4.8, 4.8, 4.6, 4.5, 4.4, 4.3, 4.2, 4.1, 4.0, 4.0, 3.9, 3.8, 3.5, 3.4 and 3.3.

In an embodiment of the invention, Salt Form A is an anhydrate (i.e. a crystalline phase that does not contain water).

In an embodiment of the invention, Salt Form A has a water uptake value of less than 1% as measured by the increase in mass determined by GVS at 80% relative humidity and 25° C.

An embodiment of the invention provides Salt Form A substantially free of other physical forms. Substantially free of other physical forms means that at least 90% by weight, e.g. 90, 91, 92, 93, 94, 95, 96, 97, 98 or 100% of the napadisylate salt is in that physical form.

The napadisylate salt of the present invention may be prepared as follows: A mixture of [2-(4-chloro-benzyloxy)-ethyl]-[2-((R)-cyclohexyl-hydroxy-phenyl-methyl)-oxazol-5-ylmethyl]dimethyl-ammonium bromide and naphthalene-1,5-disulfonate disodium salt are reacted in a suitable solvent (e.g. dichloromethane/water mixture) and stirred at a suitable temperature (e.g. 20 to 25 ° C.) for a period of time (e.g. 6 to 24 hours). Solid product may be isolated by separating the organic layer from the reaction mixture and evaporating the solvent to yield crude [2-(4-chloro-benzyloxy)-ethyl]-[2-((R)-cyclohexyl-hydroxy-phenyl-methyl)-oxazol-5-ylmethyl]-dimethyl-ammonium hemi-naphthalene-1,5-disulfonate as an amorphous solid. Alternatively, solid product may be isolated by addition of N-heptane to the reaction mixture. The mixture is stirred then allowed to stand, a further amount of dichloromethane added, and the mixture again stirred until a precipitation of solid product is obtained. The solids may then be collected and dried to yield [2-(4-chloro-benzyloxy)-ethyl]-[2-(R)-cyclohexyl-hydroxy-phenyl-methyl)-oxazol-5-ylmethyl]-dimethyl-ammonium hemi-naphthalene-1,5-disulfonate.

Salt Form A of [2-(4-chloro-benzyloxy)-ethyl]-[2-((R)-cyclohexyl-hydroxy-phenyl-methyl)-oxazol-5-ylmethyl]-dimethyl-ammonium hemi-naphthalene-1,5-disulfonate may be prepared by taking crude 4-chloro-benzyloxy)-ethyl]-[2-(R)-cyclohexyl-hydroxy-phenyl-methyl)-oxazol-5-ylmethyl]-dimethyl-ammonium hemi-naphthalene-1,5-disulfonate (e.g. as prepared by the process described herein above) and forming a slurry of the salt in acetonitrile, stirring the slurry until the slurry contains Salt Form A, and finally collecting and drying the solid. In one embodiment, the slurry is maintained at ambient temperature (e.g. 20° C.). In another embodiment, the slurry may be heated to a suitable temperature and then cooled back to ambient temperature. Alternatively, Salt Form A may be obtained by dissolving crude 4-chloro-benzyloxy)-ethyl]-[2-((R)-cyclohexyl-hydroxy-phenyl-methyl)-oxazol-5-ylmethyl]-dimethyl-ammonium hemi-naphthalene-1,5-disulfonate in acetonitrile, heating the solution for a suitable time (i.e. until the sample is in solution, e.g. from 0.5 to 48 hours), and then cooling the solution to ambient temperature (e.g. 20° C.).

Further preparations of [2-(4-chloro-benzyloxy)-ethyl]-[2-((R)-cyclohexyl-hydroxy-phenyl-methyl)-oxazol-5-ylmethyl]-dimethyl-ammonium hemi-naphthalene-1,5-disulfonate and Salt Form A are described herein below in the experimental section.

The napadisylate salt of the invention has activity as a pharmaceutical, in particular as an anticholinergic agent including a muscarinic receptor (M1, M2, and M3) antagonist, in particular a M3 antagonist. Diseases and conditions which may be treated with the salt include:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; anti-tussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;
2. bone and joints: arthritides associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;
3. pain and connective tissue remodelling of musculoskeletal disorders due to injury [for example sports injury] or disease: arthritides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritis, scleroderma, mixed connective tissue disorder, spondyloarthropathies or periodontal disease (such as periodontitis);
4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;
5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;
6. gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);
7. abdominal: hepatitis, including autoimmune, alcoholic and viral; fibrosis and cirrhosis of the liver; cholecystitis; pancreatitis, both acute and chronic;
8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);
9. allograft rejection: acute and chronic following, for example, transplantation of kidney, heart, liver, lung, bone marrow, skin or cornea or following blood transfusion; or chronic graft versus host disease;
10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;
11. other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;
12. other disorders with an inflammatory or immunological component; including acquired immune deficiency syndrome (AIDS), leprosy, Sezary syndrome, and paraneoplastic syndromes;
13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;
14. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and,
15. gastrointestinal tract: Coeliac disease, proctitis, eosinopilic gastro-enteritis, mastocytosis, Crohn's disease, ulcerative colitis, microscopic colitis, indeterminant colitis, irritable bowel disorder, irritable bowel syndrome, non-inflammatory diarrhea, food-related allergies which have effects remote from the gut, e.g., migraine, rhinitis and eczema.

Accordingly, the present invention further provides [2-(4-chloro-benzyloxy)-ethyl]-[2-((R)-cyclohexyl-hydroxy-phenyl-methyl)-oxazol-5-ylmethyl]-dimethyl-ammonium napadisylate as hereinbefore defined for use in therapy.

In another aspect, the invention provides the use of [2-(4-chloro-benzyloxy)-ethyl]-[2-((R)-cyclohexyl-hydroxy-phenyl-methyl)-oxazol-5-ylmethyl]-dimethyl-ammonium napadisylate as hereinbefore defined, in the manufacture of a medicament for use in therapy.

In the context of the present specification, the term "therapy" also includes "prophylaxis" unless there are specific indications to the contrary. The terms "therapeutic" and "therapeutically" should be construed accordingly.

A further aspect of the invention provides a method of treating a disease state in a mammal suffering from, or at risk of, said disease, which comprises administering to a mammal in need of such treatment a therapeutically effective amount of [2-(4-chloro-benzyloxy)-ethyl]-[2-((R)-cyclohexyl-hydroxy-phenyl-methyl)-oxazol-5-ylmethyl]-dimethyl-ammonium napadisylate as hereinbefore defined.

The present invention also provides [2(4-chloro-benzyloxy)-ethyl]-[2-((R)-cyclohexyl-hydroxy-phenyl-methyl)-oxazol-5-ylmethyl]-dimethyl-ammonium napadisylate for use in the treatment of chronic obstructive pulmonary disease (COPD) (such as irreversible COPD).

The present invention also provides the use of [2-(4-chloro-benzyloxy)-ethyl]-[2-((R)-cyclohexyl-hydroxy-phenyl-methyl)-oxazol-5-ylmethyl]-dimethyl-ammonium napadisylate as hereinbefore defined, in the manufacture of a medicament for use in the treatment of chronic obstructive pulmonary disease (COPD) (such as irreversible COPD).

The present invention also provides the use of [2-(4-chloro-benzyloxy)-ethyl]-[2-((R)-cyclohexyl-hydroxy-phenyl-methyl)-oxazol-5-ylmethyl]-dimethyl-ammonium napadisylate as hereinbefore defined, in the manufacture of a medicament for use in the treatment of asthma.

The present invention further provides a method of treating chronic obstructive pulmonary disease (COPD) (such as irreversible COPD), in a warm-blooded animal, such as man, which comprises administering to a mammal in need of such treatment an effective amount of [2-(4-chloro-benzyloxy)-ethyl]-[2-((R)-cyclohexyl-hydroxy-phenyl-methyl)-oxazol-5-ylmethyl]-dimethyl-ammonium napadisylate as hereinbefore defined.

In order to use a compound of the invention for the therapeutic treatment of a warm-blooded animal, such as man, said ingredient is normally formulated in accordance with standard pharmaceutical practice as a pharmaceutical composition.

For the above-mentioned therapeutic uses the dosage administered will, of course, vary with the mode of administration, the treatment desired and the disorder indicated but may typically be in the range from 0.001 mg/kg to 30 mg/kg.

The salt according to the invention may be used on its own but will generally be administered in the form of a pharmaceutical composition in which the [2-(4-chloro-benzyloxy)-ethyl]-[2-((R)-cyclohexyl-hydroxy-phenyl-methyl)-oxazol-5-ylmethyl]-dimethyl-ammonium napadisylate (active ingredient) is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition may comprise from 0.05 to 99% w (per cent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising [2-(4-chloro-benzyloxy)-ethyl]-[2-((R)-cyclohexyl-hydroxy-phenyl-methyl)-oxazol-5-ylmethyl]-dimethyl-ammonium napadisylate in association with a pharmaceutically acceptable adjuvant, diluent or carrier.

The invention further provides a process for the preparation of a pharmaceutical composition of the invention which comprises mixing [2-(4-chloro-benzyloxy)-ethyl]-[2-((R)-cyclohexyl-hydroxy-phenyl-methyl)-oxazol-5-ylmethyl]-dimethyl-ammonium napadisylate with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane (HFA) aerosols and dry powder formulations, for example, formulations in the inhaler device known as the Turbuhaler®; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

In an embodiment of the invention, the active ingredient is administered by inhalation. In a further embodiment, the active ingredient is administered by means of a dry powder inhaler. The inhaler may be a single or a multi dose inhaler, and may be a breath actuated dry powder inhaler.

When administered via inhalation the dose of the active ingredient may generally be in the range of from 0.1 µg to 10000 µg, 0.1 to 5000 µg, 0.1 to 1000 µg, 0.1 to 500 µg, 0.1 µg, 0.1 to 200 µg, 0.1 to 100 µg, 0.1 to 50 µg, 5 µg to 5000 µg, 5 to 1000 µg, 5 to 500 µg, 5 to 200 µg, 5 to 100 µg, 5 to 50 µg, 10 to 5000 µg, 10 to 1000 µg, 10 to 500 µg, 10 to 200 µg, 10 to 100 µg, 10 to 50 µg, 20 to 5000 µg, 20 to 1000 µg, 20 to 500 µg, 20 to 200 µg, 20 to 100 µg, 20 to 50 µg, 50 to 5000 µg, 50 to 1000 µg, 50 to 500 µg, 50 to 200 µg, 50 to 100 µg, 100 to 5000 µg, 100 to 1000 µg or 100 to 500 µg.

Dry powder formulations and pressurized HFA aerosols of the active ingredient may be administered by oral or nasal inhalation. For inhalation, the compound is desirably finely divided. The finely divided compound preferably has a mass median diameter of less than 10 µm, and may be suspended in a propellant mixture with the assistance of a dispersant, such as a $C_8$-$C_{20}$ fatty acid or salt thereof, (for example, oleic acid), a bile salt, a phospholipid, an alkyl saccharide, a perfluorinated or polyethoxylated surfactant, or other pharmaceutically acceptable dispersant.

One possibility is to mix the finely divided compound of the invention with a carrier substance, for example, a mono-, di- or polysaccharide, a sugar alcohol, or another polyol. Suitable carriers are sugars, for example, lactose, glucose, raffinose, melezitose, lactitol, maltitol, trehalose, sucrose, mannitol and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure. This spheronized powder may be filled into the drug reservoir of a multidose inhaler, for example, that known as the Turbuhaler® in which a dosing unit meters the desired dose which is then inhaled by the patient. With this system the active ingredient, with or without a carrier substance, is delivered to the patient.

For oral administration the compound of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compound of the invention may be admixed with, for example, a vegetable oil or polyethylene glycol. Hard gelatine capsules may contain granules of the compound using either the above-mentioned excipients for tablets. Also liquid or semisolid formulations of the compound of the invention may be filled into hard gelatine capsules.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, saccharine and/or carboxymethylcellulose as a thickening agent or other excipients known to those skilled in art.

The invention will now be illustrated by the following non-limiting Examples. In the Examples the following Figures are presented:

FIG. 1: X-ray powder diffraction pattern of salt Form A of [2-(4-chloro-benzyloxy)-ethyl]-[2-((R)-cyclohexyl-hydroxy-phenyl-methyl)-oxazol-5-ylmethyl]-dimethyl-ammonium hemi-naphthalene-1,5-disulfonate.

Synthesis of [2-(4-chloro-benzyloxy)-ethyl]-[2-((R)-cyclohexyl-hydroxy-phenyl-methyl)-oxazol-5-ylmethyl]-dimethyl-ammonium hemi-naphthalene-1,5-disulfonate Preparation [1]

General Experimental Details for Preparation [1]

All reactions were carried out under an atmosphere of nitrogen unless specified otherwise.

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz. Shifts are given in ppm relative to tetramethylsilane.

Where products were purified by column chromatography, 'flash silica' refers to silica gel for chromatography, 0.035 to 0.070 mm (220 to 440 mesh) (e.g. Fluka silica gel 60), and an applied pressure of nitrogen up to 10 p.s.i accelerated column elution. Where thin layer chromatography (TLC) has been used, it refers to silica gel TLC using plates, typically 3×6 cm silica gel on aluminium foil plates with a fluorescent indicator (254 nm), (e.g. Fluka 60778). All solvents and commercial reagents were used as received.

All compounds containing a basic centre(s), which were purified by HPLC, were obtained as the TFA salt unless otherwise stated.

Preparative HPLC Conditions:

C18-reverse-phase column (100×22.5 mm i.d. Genesis column with 7 µm particle size). UV detection at 230 nm.

LC/MS Systems

The Liquid Chromatography Mass Spectroscopy (LC/MS) systems used:

LC-MS Method 1

Waters Platform LCT with a C18-reverse-phase column (100×3.0 mm Higgins Clipeus with 5 µm particle size), elution with A: water+0.1% formic acid; B: acetonitrile+0.1% formic acid. Gradient:

| Gradient - Time | flow mL/min | % A | % B |
| --- | --- | --- | --- |
| 0.00 | 1.0 | 95 | 5 |
| 1.00 | 1.0 | 95 | 5 |
| 15.00 | 1.0 | 5 | 95 |
| 20.00 | 1.0 | 5 | 95 |
| 22.00 | 1.0 | 95 | 5 |
| 25.00 | 1.0 | 95 | 5 |

Detection—MS, ELS, UV (100 µl split to MS with in-line UV detector at 254 nm) MS ionisation method—Electrospray (positive ion)

LC-MS Method 2

Waters Micromass ZQ with a C18-reverse-phase column (30×4.6 mm Phenomenex Luna 3 µm particle size), elution with A: water+0.1% formic acid; B: acetonitrile+0.1% formic acid. Gradient:

| Gradient - Time | flow mL/min | % A | % B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (100 µl split to MS with in-line UV detector) MS ionisation method—Electrospray (positive and negative ion)

Abbreviations Used in Preparation [1]:
Aq=aqueous
DCM=dichloromethane
DMF=dimethylformamide
EtOAc=ethyl acetate
EtOH=ethanol
GVS=Gravimetric vapour sorption
MeOH=methanol
RT=RT
Rt=retention time
THF=tetrahydrofuran
Satd=saturated The following intermediates 1-7 were used in preparation [1] of 1 [2-(4-chloro-benzyloxy)-ethyl]-[2-((R)-cyclohexyl-hydroxy-phenyl-methyl)-oxazol-5-ylmethyl]-dimethyl-ammonium hemi-naphthalene-1,5-disulfonate.

Intermediate 1:
2-Oxo-2-phenyl-N-prop-2-ynyl-acetamide

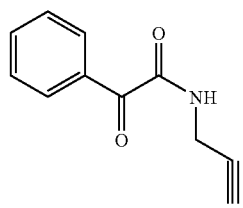

Oxalyl chloride (6.1 g, 48 mmol) was added to a solution of phenylglyoxylic acid (6.0 g, 40 mmol) and 3 drops of DMF in dry DCM (50 mL). The reaction mixture was stirred at RT for 3 h then the solvent was removed. The residue was taken up in dry DCM (50 mL) and the solution was cooled to 0° C. A mixture of propargyl amine (2.2 g, 40 mmol) and triethylamine (4.05 g, 40 mmol) was added cautiously over a period of 10 min then the mixture was allowed to warm to RT. Stirring was continued for 2.5 h then water (10 mL) was added. The mixture was washed with 1 M HCl, sat. sodium hydrogencarbonate (aq.), then brine. The organic phase was then dried (Na$_2$SO$_4$) and the solvent was removed. The residue was crystallized from cyclohexane to afford the product as a light brown solid.

Yield: 5.75 g, 76%. LC-MS Method 2: Rt 2.47 min, m/z 188 [MH$^+$].

Intermediate 2:
(5-Methyl-oxazol-2-yl)-phenyl-methanone

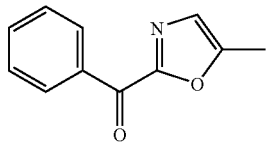

Methane sulfonic acid (10 g, 104 mmol) was added drop wise to a solution of 2-oxo-2-phenyl-N-prop-2-ynyl-acetamide (Intermediate 1) (2.4 g, 12.83 mmol) in 1,4-dioxane (20 mL). The resultant solution was heated at 90° C. for 66 h. The reaction mixture was cooled and the solvent was removed. The dark residue was partitioned between DCM and water. The DCM fraction was washed with 1 M HCl (2×), satd. sodium hydrogencarbonate solution (aq., 2×), then brine. The solution was dried (Na$_2$SO$_4$) and the solvent was removed to give the crude product. Purification was achieved via column chromatography, eluting with cyclohexane/EtOAc (4:1). This afforded the product as an off-white solid.

Yield: 1.0 g, 41%. LC-MS Method 2: Rt 2.94 min, m/z 188 [M$^+$].

Intermediate 3:
Cyclohexyl-(5-methyl-oxazol-2-yl)-phenyl-methanol

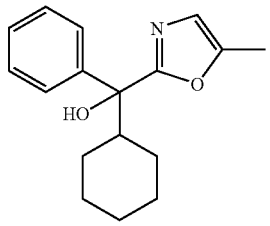

A solution of (5-methyl-oxazol-2-yl)-phenyl-methanone (intermediate 2) (3.0 g, 16 mmol) in 32 mL dry THF at 0° C. under nitrogen was treated dropwise over 10 min with a 2 M solution of cyclohexylmagnesium chloride in diethyl ether (10 mL, 20 mmol). The resulting deep yellow solution was stirred at 0° C. for about 30 min during which time a precipitate was formed, and then at RT for 1.5 h. The reaction mixture was cooled to 0° C. again and treated cautiously with satd. ammonium chloride solution (aq.). The mixture was stirred at RT for 10 min then diluted with water (10 mL). The phases were separated and the organic phase was washed with brine. The combined aqueous phase was extracted with DCM and the combined organic phase was dried (MgSO$_4$) and concentrated in vacuo to give the crude product, which was triturated with ether, filtered off and dried.

Yield: 3.65 g, 84%. LCMS Method 2: Rt 3.78 min, m/z 272 [MH$^+$].

Intermediate 4: (5-Bromomethyl-oxazol-2-yl)-cyclohexyl-phenyl-methanol

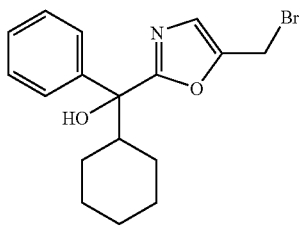

A solution of cyclohexyl-(5-methyl-oxazol-2-yl)-phenyl-methanol (Intermediate 3) (3.0 g, 11.1 mmol) in 1,2-dichloroethane (22 mL) was treated with N-bromo-succinimide (2.16 g, 12.2 mmol) followed by 2,2'-azobis(2-methylpropionitrile) (0.18 g, 2.1 mmol). The mixture was heated to 80° C. for 2.5 h and then allowed to cool to RT. Satd. sodium hydrogen carbonate solution (aq.) was added and the phases were separated. The organic layer was washed with brine and the combined aqueous layers were extracted with DCM. The combined organic phase was dried (MgSO$_4$) and concentrated in vacuo to give the crude product as a brown oil. Purification was achieved via column chromatography eluting with 33-100% DCM/cyclohexane, followed by 25% EtOAc/DCM.

Yield: 1.85 g, 48%. LCMS Method 2: Rt 4.27 min, m/z 350, 352 [MH$^+$].

Intermediate 5: Cyclohexyl-(5-dimethylaminomethyl-oxazol-2-yl)-phenyl-methanol

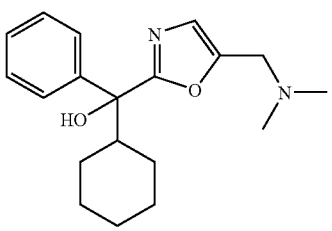

A solution of (5-bromomethyl-oxazol-2-yl)-cyclohexyl-phenyl-methanol (Intermediate 4) (3.2 g, 9.2 mmol) in THF (40 mL) was treated with a 2 M solution of dimethylamine in THF (40 mL, 80 mmol). A suspension formed after stirring for a few minutes. The reaction mixture was left at RT overnight and then the solid was filtered off and discarded. The filtrate was concentrated under reduced pressure and the residue was partitioned between DCM and satd. sodium hydrogen carbonate solution (aq.). The organic layer was dried (Na$_2$SO$_4$) and evaporated to afford the title compound as a solid.

Yield: 2.74 g, 95%.
LC-MS (Method 1): Rt 6.57 min, m/z 315 [MH$^+$].

$^1$H NMR (DMSO-d$_6$): δ 0.92-1.29 (m, 6H), 1.42-1.74 (m, 4H), 2.10 (s, 6H), 2.22 (m, 1H), 3.45 (s, 2H), 5.90 (s, 1H), 6.98 (s, 1H), 7.18-7.22 (m, 1H), 7.27-7.34 (m, 2H), 7.40-7.46 (m, 2H) ppm.

The two enantiomers of cyclohexyl-(5-dimethylaminomethyl-oxazol-2-yl)-phenyl-methanol (Intermediate 5) (2.74 g) were separated by preparative chiral HPLC using a 250×20 mm Chiralpak® IA column packed with amylase tris(3,5-dimethylphenyl-carbamate) immobilized on 5 μm silica gel. The column was eluted with 5% EtOH in heptane buffered with 0.1% diethylamine at 15 mL/min. The first eluting enantiomer (Rt 8.5 min) afforded (S)-cyclohexyl-(5-dimethylaminomethyl-oxazol-2-yl)-phenyl-methanol (Intermediate 5a) as a white solid.

Intermediate 5a: (S)-cyclohexyl-(5-dimethylaminomethyl-oxazol-2-yl)-phenyl-methanol

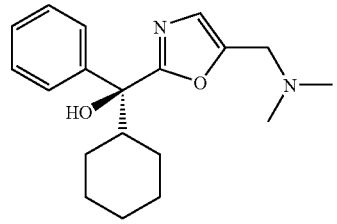

Yield: 0.73 g, 27%.
LC-MS (Method 1): Rt 6.50 min, m/z 315 [MH$^+$].
$^1$H NMR (CDCl$_3$): δ 1.12-1.39 (m, 7H), 1.62-1.76 (m, 3H), 2.25 (s, 6H), 2.29-2.32 (m, 1H), 3.54 (dd$_{AB}$, 2H), 3.70 (br.s, 1H), 6.84 (s, 1H), 7.24 (t, 1H), 7.33 (t, 2H), 7.64 (d, 2H) ppm.

The second eluting enantiomer (Rt 10.3 min) afforded (R)-cyclohexyl-(5-dimethylaminomethyl-oxazol-2-yl)-phenyl-methanol (Intermediate 5b) as a white solid.

Intermediate 5b: (R)-cyclohexyl-(5-dimethylaminomethyl-oxazol-2-yl)-phenyl-methanol

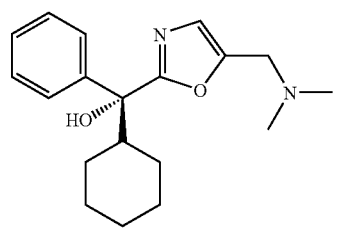

Yield: 1.04 g, 38%.
LC-MS (Method 1): Rt 6.48 min, m/z 315 [MH$^+$].
$^1$H NMR (CDCl$_3$): δ 1.10-1.39 (m, 7H), 1.62-1.76 (m, 3H), 2.25 (s, 6H), 2.29-2.35 (m, 1H), 3.54 (dd$_{AB}$, 2H), 3.70 (br.s, 1H), 6.84 (s, 1H), 7.24 (t, 1H), 7.33 (t, 2H), 7.64 (d, 2H) ppm.

Intermediate 6: Methanesulfonic acid 2-(4-chloro-benzyloxy)-ethyl ester

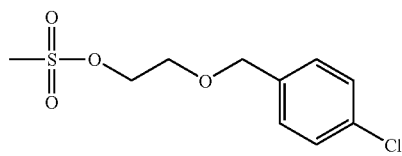

A solution of methanesulfonyl chloride (980 µL, 12.6 mmol) in dry DCM (10 mL) was slowly added to a cooled (0° C.) solution of 2-(4-chloro-benzyloxy)-ethanol (2.14 g, 11.46 mmol) and diisopropylethylamine (2.0 mL, 23 mmol) in dry DCM (10 mL). The reaction mixture was allowed to warm to RT overnight. Water was added and the organic layer was dried (MgSO$_4$) and concentrated. The residue was purified by column chromatography over silica using a gradient of 0-20% diethyl ether/cyclohexane to afford the pure product.

Yield: 1.87 g, 67%.

$^1$H NMR (CDCl$_3$): δ3.03 (s, 3H), 3.74 (m, 2H), 4.39 (m, 2H), 4.54 (s, 2H), 7.27 (d, 2H), 7.33 (d, 2H) ppm.

Intermediate 7:
1-(2-Bromo-ethoxymethyl)-4-chloro-benzene

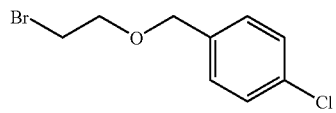

A mixture of methanesulfonic acid 2-(4-chloro-benzyloxy)-ethyl ester (Intermediate 6) (1.37 g, 5.18 mmol) and lithium bromide (1.80 g, 20.7 mmol) in acetone (15 mL) was heated at reflux overnight. The reaction mixture was concentrated to dryness and the residue partitioned between DCM and water. The organic layer was dried (MgSO$_4$), and concentrated, and purified by column chromatography over silica using DCM/cyclohexane (1:3) as eluent to afford the product as a colourless oil.

Yield: 0.67 g, 78%.

$^1$H NMR (CDCl$_3$): δ3.49 (t, 2H), 3.79 (t, 2H), 4.55 (s, 2H), 7.30 (d, 2H), 7.32 (d, 2H), ppm.

Intermediate 8: [2-(4-Chloro-benzyloxy)-ethyl]-[2-(R)-cyclohexyl-hydroxy-phenyl-methyl)-oxazol-5-ylmethyl]-dimethyl-ammonium bromide A solution of (R)-cyclohexyl-(5-dimethylaminomethyloxazol-2-yl)-phenyl-methanol (Intermediate 5b) (0.40 g, 1.27 mmol) and 1-(2-bromo-ethoxymethyl)-4-chloro-benzene (Intermediate 7) (0.67 g, 2.68 mmol) in chloroform (4 mL) and acetonitrile (4 mL) was heated at 50° C. for 3 days. The reaction mixture was concentrated to dryness to afford a yellow oil, which was purified by column chromatography eluting with 2.5-25% MeOH/DCM to afford the product as a white foam. Yield, 0.68 g, 92%

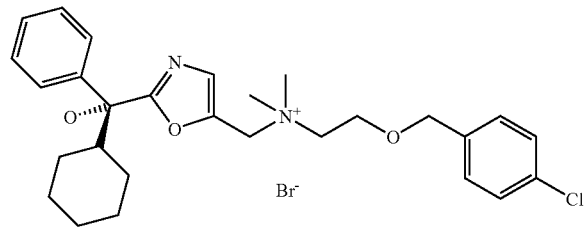

LC-MS (Method 1): Rt 8.72 min, ink 483 [M$^+$].

$^1$H NMR (CDCl$_3$): δ1.08-1.40 (m, 7H), 1.61-1.76 (m, 3H), 2.31 (m, 1H), 3.32 (s, 6H), 3.88 (m, 2H), 3.94 (m, 2H), 4.03 (br. s, 1H), 4.54 (s, 2H), 5.17 (dd$_{AB}$, 2H), 7.21-7.26 (m, 3H), 7.28-7.34 (m, 4H), 7.46 (s, 1H), 7.56 (d, 2H) ppm.

[2-(4-chloro-benzyloxy)-ethyl]-[2-((R)-cyclohexyl-hydroxy-phenyl-methyl)-oxazol-5-ylmethyl]-dimethyl-ammonium hemi-naphthalene-1,5-disulfonate Preparation [1]

A mixture of [2-(4-chloro-benzyloxy)-ethyl]-[2-((R)-cyclohexyl-hydroxy-phenyl-methyl)-oxazol-5-ylmethyl]dimethyl-ammonium bromide (0.20 g, 0.36 mmol), (Intermediate 8), naphthalene-1,5-disulfonate disodium salt (0.059 g, 0.18 mmol), DCM (2.8 mL), and water (2.8 mL) was stirred vigorously at RT overnight. N-heptane (1.0 mL) was added and the mixture was stirred vigorously. On standing two clear layers and a yellow oil were obtained. DCM (1.0 mL) was added (causing the oil to dissolve) and the mixture was stirred at RT overnight resulting in precipitation of a white solid. The solid was collected by filtration, washed with DCM/water mixture, and dried under vacuum at 50° C.

$^1$H NMR showed a spectrum corresponding to the hemi-salt (2:1 ratio of cation/anion).

Yield: 0.17 g, 77%.

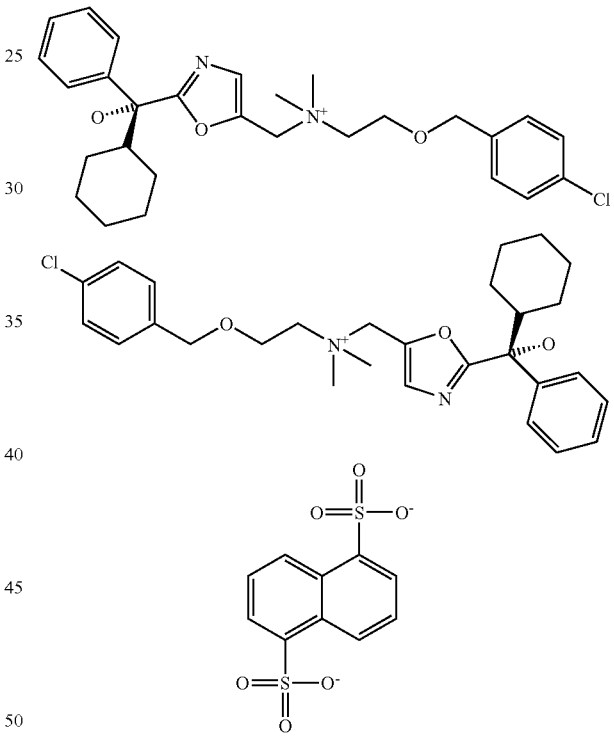

LC-MS (Method 1): Rt 8.62 min, m/z 483 [M$^+$].

$^1$H NMR (CD$_3$OD): δ 1.04-1.37 (m, 12H), 1.53 (m, 2H), 1.64-1.76 (m, 6H), 2.38 (m, 2H), 3.03 (s, 12H), 3.46 (m, 4H), 3.85 (m, 4H), 4.52 (s, 4H), 4.70 (s, 4H), 7.24 (m, 2H), 7.34 (m, 12H), 7.43 (s, 2H), 7.52 (m, 6H), 8.20 (d, 2H), 9.02 (d, 2H) ppm.

'Salt Form A' of [2-(4-chloro-benzyloxy)-ethyl]-[2-((R)-cyclohexyl-hydroxy-phenyl-methyl)-oxazol-5-ylmethyl]-dimethyl-ammonium hemi-naphthalene-1, 5-disulfonate

[2-(4-chloro-benzyloxy)-ethyl]-[2-((R)-cyclohexyl-hydroxy-phenyl-methyl)-oxazol-5-ylmethyl]-dimethyl-ammonium hemi-naphthalene-1,5-disulfonate (as prepared herein above) (107 mg, 0.17 mmol) was dissolved in the minimum quantity of MeCN at RT. The solution was heated and then allowed to cool back to RT. The resulting crystalline solid was filtered off and dried under vacuum. Yield: 83 mg, 78%. Analysis of product prepared by this route was by XRPD identified the product as 'Salt Form A'.

Preparation [2]

General Experimental Conditions for Preparation [2]

All reactions were carried out under an atmosphere of inert gas unless specified otherwise.

NMR spectra were obtained on a Bruker AVANCE400 spectrometer: Frequency: 400 MHz; 2-Channel; z-Gradient. Temp Range: 0-120° C.

HPLC Conditions:

Phenomenex Luna C18(2) column (50×4.6 mm), 3 μm particle size. UV detection at 210 nm. Elution with A: water+ 0.05% Trifluoroacetic acid; B: acetonitrile+0.05% Trifluoroacetic acid. Gradient:

| Gradient - Time | flow mL/min | % A | % B |
| --- | --- | --- | --- |
| 0.00 | 1.0 | 90 | 10 |
| 8.00 | 1.0 | 10 | 90 |
| 9.00 | 1.0 | 10 | 90 |
| 9.50 | 1.0 | 90 | 10 |
| 12.00 | 1.0 | 90 | 10 |

LC-MS Method: LC-Method as given above. MS:HP-1100 MSD. Detection—API-ES, positive mode.

Preparation [2]

A mixture of (R)-cyclohexyl-(5-dimethylaminomethyloxazol-2-yl)-phenyl-methanol[1] (1 eq.) and 1-(2-bromoethoxymethyl)-4-chloro-benzene (2 eq) in 2-propanol (5 Vol.) was heated at 52° C. for 164 h. HPLC showed a conversion of 98%. The reaction mixture was evaporated to dryness to yield [2-(4-chloro-benzyloxy)-ethyl]-[2-((R)-cyclohexyl-hydroxy-phenyl-methyl)-oxazol-5-ylmethyl]dimethyl-ammonium bromide. The crude sample of [2-(4-chloro-benzyloxy)-ethyl]-[2-((R)-cyclohexyl-hydroxy-phenyl-methyl)-oxazol-5-ylmethyl]-dimethyl-ammonium bromide was dissolved in dichloromethane (4.98 Vol.) and a solution of 1,5-naphthalene disulfonic acid di-sodium salt (1 eq.) in water (10 Vol.) added at room temperature over a period of 10 min. The mixture was diluted with dichloromethane (4.98 Vol.) and stirred for 1 hour at room temperature. The stirrer was turned off and the emulsion settled before separation. To the organic layer was added a mixture of tert-Butyl Methyl Ether (tBME) (10 Vol.) and 2-propanol (1.6 Vol.) at room temperature over a period of 72 min. The resulting suspension was filtered and the cake rinsed with tBME (2.15 Vol.). Drying (rotary evaporator at a bath temperature of 40-50° C. at 5-10 mbar) gave [2-(4-chloro-benzyloxy)-ethyl]-[2-((R)-cyclohexyl-hydroxy-phenyl-methyl)-oxazol-5-ylmethyl]-dimethyl-ammonium hemi-naphthalene-1,5-disulfonate. The yield obtained by this preparation using 130 g of (R)-cyclohexyl-(5-dimethylaminomethyloxazol-2-yl)-phenyl-methanol was 216 g, 83%. $^1$H NMR showed a spectrum corresponding to the hemi-salt (2:1 ratio of cation/anion).

Conversion to 'Salt Form A' was achieved by suspending a crude batch of [2-(4-chloro-benzyloxy)-ethyl]-[2-((R)-cyclohexyl-hydroxy-phenyl-methyl)-oxazol-5-ylmethyl]-dimethyl-ammonium hemi-naphthalene-1,5-disulfonate as prepared above in acetonitrile (13.8 Vol.). The suspension was heated to reflux and stirred at reflux for 1 hour. Then the suspension was cooled to 70° C. and stirred at this temperature over night. The suspension was cooled to room temperature and the solid filtered and washed with acetonitrile (1.4 Vol.) and dried (rotary evaporator at a bath temperature of 40-50° C. at 5-10 mbar) to yield 'Salt Form A'. The yield obtained by this conversion using 216 g of crude [2-(4-chloro-benzyloxy)-ethyl]-[2-((R)-cyclohexyl-hydroxy-phenyl-methyl)-oxazol-5-ylmethyl]-dimethyl-ammonium heminaphthalene-1,5-disulfonate as starting material was 203.5 g, 94%.

[1] (R)-cyclohexyl-(5-dimethylaminomethyloxazol-2-yl)-phenyl-methanol is Intermediate 5b as described herein above in Preparation [1]. An alternative preparation of (R)-cyclohexyl-(5-dimethylaminomethyloxazol-2-yl)-phenyl-methanol, is as follows.

(R)-cyclohexyl-(5-dimethylaminomethyl-oxazol-2-yl)-phenyl-methanol (5-Dimethylaminomethyl-oxazo-2-yl)-phenyl-methanone[2] was dissolved in THF (8.4 L/kg) and cooled to a temperature of 0±5° C., to which cyclohexyl magnesium chloride (1.3 eq., as a 20 w/w% solution in Toluene/THF) was dosed over at least 1 hour (h). The reaction mixture was heated to 20° C. over 40 min and stirred at 20° C. for at least 1 h, at which point conversion to product was >96% by HPLC. The reaction mixture was dosed to a mixture of 23.1 w/w % NH$_4$Cl (3.97 L/kg) and water (3.97 L/kg). The phases were separated and the aqueous layer extracted with ethyl acetate (7 L/kg). The combined organic layers were washed with water (5.25 L/kg), and 70% of the volume removed by distillation (p≧130 mbar, 50° C.). To the distillation residue acetonitrile (7.82 L/kg) was added and the suspension heated until complete dissolution was attained (70° C.). The reaction was then cooled to 0° C. over 7 h and stirred at 0° C. for at least 1 h. The reaction product (±)-cyclohexyl-(5-dimethylaminomethyl-oxazol-2-yl)-phenyl-methanol was then collected by filtration and washed three times with cold acetonitrile (1.65 L/kg). Yields achieved with this procedure ranged between 60-70% and the purities achieved were >97% peak area (HPLC) and >97% w/w (NMR). (R)-Cyclohexyl-(5-dimethylaminomethyl-oxazol-2-yl)-phenyl-methanol was separated from this racemic mixture by chiral SMB chromatography on a Chiralpak AD column using acetonitrile:isopropanol:diethylmethylamine (90:10:0.1) as eluent.

[2] A preparation of (5-dimethylaminomethyl-oxazo-2-yl)-phenyl-methanone is described in WO 2007/017669 (intermediate 4).

Preparation [3]

General Experimental Conditions for Preparation [3] are the same as for Preparation [2]

A mixture of (R)-cyclohexyl-(5-dimethylaminomethyloxazol-2-yl)-phenyl-methanol (1 eq.) and 1-(2-bromoethoxymethyl)-4-chloro-benzene (2 eq.) in 2-propanol (5 Vol.) was submitted to the following temperature program:

Heat to 70° C. (internal temperature) over 1 hour, stir at 70° C. for 26 hours and then cool to 20° C. over 30 minutes. The conversion is checked by HPLC.

The reaction mixture was evaporated to dryness (rotary evaporator at a bath temperature of 40-50° C. at 10-15 mbar) and the residue dissolved in dichloromethane (8.9 Vol.). To the is solution was added a solution of 1,5-naphthalene disulfonic acid di-sodium salt (1 eq.) in water (17.7 Vol.) over at least 10 minutes. The resulting mixture was diluted with dichloromethane (8.9 Vol.) and stirring continued at room temperature for 1 hour. The stirrer was turned off and the emulsion settled before separation. To the organic layer was added, over a period of at least 60 minutes at room temperature, a mixture of tBME (17.7 Vol.) and 2-propanol (2.86 Vol.). The suspension formed was stirred at room temperature for 10 to 60 minutes and then filtered. The filter cake is washed with tBME (2×3.46 Vol.) and dried (rotary evaporator at a bath temperature of 40-50° C. at 5-10 mbar) until a Loss On Drying (LOD) ≦2 w/w % is obtained. The material was suspended in (22.9 Vol.) of acetonitrile and the suspension submitted to the following temperature program:

Heat to reflux over a period of at least 30 minutes. Stir at reflux for 60 to 70 minutes, then cool to 70° C. (internal temperature) and stir at 70° C. for 16 to 24 hours and finally cool to 20° C. over 1 hour. The suspension was filtered and the filter cake washed with acetonitrile (4.61 Vol.). The material was dried (rotary evaporator at a bath temperature of 40-50° C. at 5-10 mbar) until a LOD ≦1 w/w % is obtained.

The yield obtained by this preparation using 25.0 g of (R)-cyclohexyl-(5-dimethylaminomethyloxazol-2-yl)-phenyl-methanol was 38.7 g, 78%.

The yield obtained by this preparation using 129.9 g of (R)-cyclohexyl-(5-dimethylaminomethyloxazol-2-yl)-phenyl-methanol was 203.6 g, 79%. HPLC and NMR showed a spectrum corresponding to the hemi-salt (2:1 ratio of cation/anion).

Solid State Analysis of Salt Form A of [2-(4-chloro-benzyloxy)-ethyl]-[2-((R)-cyclohexyl-hydroxy-phenyl-methyl)-oxazol-5-ylmethyl]-dimethyl-ammonium hemi-naphthalene-1,5-disulfonate 'Salt Form A' prepared according to Preparation [2] was tested as follows.

Instrument Details
  XRPD—PANalytical CubiX PRO machine in Ø-Ø configuration over the scan range 2° to 40° 2Ø with 100-second exposure per 0.02° increment. The X-rays were generated by a copper long-fine focus tube operated at 45 kV and 40 mA. The wavelength of the copper X-rays was 1.5418 Å. The Data was collected on zero background holders on which ~2 mg of the compound was placed. The holder was made from a single crystal of silicon, which had been cut along a non-diffracting plane and then polished on an optically flat finish. The X-rays incident upon this surface were negated by Bragg extinction.
  DSC thermograms were measured using a TA Q1000 Differential Scanning Calorimeter, with aluminium pans and pierced lids. The sample weights varied between 0.5 to 5 mg. The procedure was carried out under a flow of nitrogen gas (50 ml/min) and the temperature studied from 25 to 300° C. at a constant rate of temperature increase of 10° C. per minute.
  TGA thermograms were measured using a TA Q500 Thermogravimetric Analyser, with platinum pans. The sample weights varied between 1 and 5 mg. The procedure was carried out under a flow of nitrogen gas (60 ml/min) and the temperature studied from 25 to 200° C. at a constant rate of temperature increase of 10° C. per minute.
  GVS profiles were measured using a Dynamic Vapour Sorption DVS-1 instrument. The solid sample ca. 1-5 mg was placed into a glass vessel and the weight of the sample was recorded during a dual cycle step method (40 to 90 to 0 to 90 to 0% relative humidity (RH), in steps of 10% RH) at 25° C.

The melting temperature of Form A as determined by DSC was found to be 233° C. (onset) (±3° C.). Weight loss observed prior to melting by TGA was very low (from 0.0% -0.5%). GVS determination gave a weight increase of less than 0.5% (% w/w) at 80% RH (±0.3%).

An XRPD spectrum of 'Salt Form A' is presented in FIG. 1.

'Salt Form A' was Micronised in a 50 mm jet mill, with ejector pressure 5 bar and milling pressure 1.5-2 bar, giving (90% yield). Particle size of the micronised material as determined by Malvern Laser Diffraction with dry powder feeder was d(0.1) 0.77 µm: d(0.5), 1.45µ: d(0.9): 2.65 µm. An investigational evaluation of the deaggregation properties of micronised 'Salt Form A' showed excellent Fine Particle Fraction (FPF>60%) across a range of relative humidity (0-75% RH).

Biological Activity of [2-(4-chloro-benzyloxy)-ethyl]-[2-((R)-cyclohexyl-hydroxy-phenyl-methyl)-oxazol-5-ylmethyl]-dimethyl-ammonium The inhibitory effects of compounds of the napadisylate salt were determined by a Muscarinic Receptor Radioligand Binding Assay. Radioligand binding studies were carried out in Scintillation Proximity Assay (SPA) format utilising [3H]-N-methyl scopolamine ([3H]-NMS) and cell membranes expressing the human muscarinic receptors (M2 or M3) which were coated onto SPA beads. Coated SPA beads were incubated in 96-well plates in HEPES buffer with [3H]-NMS and M3 antagonist at various concentrations for 16 hours. Radioligand binding was then counted using a Wallac Microbeta scintillation counter. [2-(4-Chloro-benzyloxy)-ethyl]-[2-(R)-cyclohexyl-hydroxy-phenyl-methyl)-oxazol-5-ylmethyl]-dimethyl-ammonium displayed a M3 binding $pIC_{50}$ of 9.8.

The invention claimed is:

1. A salt being [2-(4-chloro-benzyloxy)-ethyl]-[2-((R)-cyclohexyl-hydroxy-phenyl-methyl)-oxazol-5-ylmethyl]-dimethyl-ammonium napadisylate.

2. A salt according to claim 1 which is [2-(4-chloro-benzyloxy)-ethyl]-[2-((R)-cyclohexyl-hydroxy-phenyl-methyl)-oxazol-5-ylmethyl]-dimethyl-ammonium hemi-naphthalene-1,5-disulfonate.

3. A salt according to claim 2, which exhibits at least the following characteristic X-ray powder diffraction peaks (expressed in degrees 2θ): 5.3, 10.5, 15.8, and 16.5.

4. A salt according to claim 3 having an X-ray powder diffraction pattern substantially the same as that shown in FIG. 1.

5. A salt according to claim 1, wherein the salt is an anhydrate.

6. A pharmaceutical composition, wherein the composition comprises:
  a salt according to claim 1, and
  a pharmaceutically acceptable adjuvant, diluent, or carrier.

7. A method of treating chronic obstructive pulmonary disease, wherein the method comprises administering a salt according to claim 1 to a patient in need of such treatment.

8. A pharmaceutical composition, wherein the composition comprises:
  a salt according to claim 2, and
  a pharmaceutically acceptable adjuvant, diluent, or carrier.

9. A method of treating chronic obstructive pulmonary disease, wherein the method comprises administering a salt according to claim 2 to a warm-blooded animal in need of such treatment.

10. A method according to claim 9, wherein the warm-blooded animal is a human.

11. A salt according to claim 2, which exhibits at least the following characteristic X-ray powder diffraction peaks (expressed in degrees 2θ): 5.3, 10.5, 15.8, 16.5, 18.6 and 19.4.

12. A salt according to claim 2, which exhibits at least the following characteristic X-ray powder diffraction peaks (expressed in degrees 2θ): 5.3, 10.5, 15.8, 16.5, 18.6, 19.4, 19.7.

13. A salt according to claim 2, which exhibits at least the following characteristic X-ray powder diffraction peaks (expressed in degrees 2θ): 5.3, 10.5, 15.8, 16.5, 17.8, 18.6, 19.4, 19.7, 20.4 and 21.7.

14. A salt according to claim 2, wherein the salt is an anhydrate.

15. A pharmaceutical composition, wherein the composition comprises:
   a salt according to claim 14, and
   a pharmaceutically acceptable adjuvant, diluent, or carrier.

16. A method of treating chronic obstructive pulmonary disease, wherein the method comprises administering a salt according to claim 14 to a warm-blooded animal in need of such treatment.

17. A method according to claim 16, wherein the warm-blooded animal is a human.

18. A pharmaceutical composition, wherein the composition comprises:
   a salt according to claim 5, and
   a pharmaceutically acceptable adjuvant, diluent, or carrier.

19. A method of treating chronic obstructive pulmonary disease, wherein the method comprises administering a salt according to claim 5 to a warm-blooded animal in need of such treatment.

20. A method according to claim 19, wherein the warm-blooded animal is a human.

* * * * *